United States Patent [19]

Drewlow

[11] Patent Number: Plant 7,097

[45] Date of Patent: Jan. 9, 1990

[54] IMPATIENS PLANT NAMED NEBULOUS

[75] Inventor: Lyndon W. Drewlow, Ashtabula, Ohio

[73] Assignee: Mikkelsens, Inc., Ashtabula, Ohio

[21] Appl. No.: 308,818

[22] Filed: Feb. 9, 1989

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

An Impatiens plant named Nebulous, having large, salmon orange flowers, reddish green leaves, dense branching, early flowering, good tolerance to both high and low temperatures, and a floriferous habit.

1 Drawing Sheet

The present invention relates to a new and distinctive cultivar of Impatiens plant, botanically known as Impatiens, and known by the cultivar name Nebulous. The new cultivar was developed by me through controlled breeding by crossing Mikkelsen Seedling No. 86-308-2 (seed parent) with Mikkelsen Seedling No. 86-196-3 (pollen parent). Asexual reproduction by terminal or stem cuttings has shown that the unique features of this new impatiens are stabilized and are reproduced true to type in successive propagations.

The following characteristics distinguish the new impatiens from its parent varieties and other cultivated impatiens of this type known and used in the floriculture industry. Certain characteristics are more meaningful by reference to known cultivars. References are made to Eclipse, U.S. Plant Pat. No. 4,689; Quasar, U.S. Plant Pat. No. 5,780; Nova, U.S. Plant Pat. No. 6,004; Sunset and Eurema.

1. Flower color of Nebulous is a deeper shade of salmon orange than Quasar but not as deep as Sunset and Eurema, with Eclipse and Nova being a bright orange.

2. Flower size of Nebulous is larger than any of the comparison cultivars.

3. Nebulous has reddish green leaves that are darker in color than Eurema but not as dark as Nova and Eclipse. Sunset and Quasar have bright green leaves.

4. Upper leaf surface of Nebulous is slightly hirsute similar to Eclipse, with Nova and Eurema being more hirsute. Quasar and Sunset have glabrous upper surfaces.

5. Nebulous is a densely branched semi-compact plant, with Sunset and Nova being more compact, Quasar similar in size but more upright, and Eurema and Eclipse larger plants, with Eclipse having an open growth habit.

6. Nebulous is not variegated, similar to Eclipse, while Quasar shows slight variegation and Eurema, Nova, and Sunset have moderate to heavy variegation depending on light levels.

7. Flower pedicels of Nebulous are greenish yellow in color and glabrous, while the pedicels of Eurema are greenish yellow and hirsute. The pedicels of Nova, Eclipse, and Quasar have a slight reddish tint, and Sunset has reddish purple pedicels. Nova also has hirsute pedicels while the rest are glabrous.

8. Nebulous, Nova and Eclipse have a red midrib and venation while Eurema, Sunset and Quasar have only a slight red tint to the midrib.

9. Immature flower buds are reddish in color for Nebulous, Nova, Eurema, and Eclipse, with Sunset having some red tint on buds and Quasar having only a trace of red.

10. Leaf size of Nebulous is similar to Sunset, Eurema and Eclipse, although the leaves of Eclipse are somewhat narrower. Quasar and Nova have longer and narrower leaves.

11. Flowering of Nebulous is earlier than Eclipse by 10 days, Nova and Sunset by 5 to 7 days, and similar to Quasar and Eurema.

12. Stems are glabrous for Nebulous, Eclipse, Sunset and Quasar, while Eurema and Nova have hirsute stems.

13. Immature pistils of Nebulous and Eurema have reddish stigmas and styles and mostly green ovaries, while Eclipse and Nova have reddish purple stigmas, styles and ovaries, and Quasar and Sunset have yellowish green stigmas and styles and green ovaries.

14. Flower spurs of Nebulous, Eurema and Quasar have a moderate red tint while Sunset, Nova, and Eclipse have deep red spurs.

15. Nebulous has shown tolerance to both high and low temperatures (40° to 50° F.) thus expanding the growing season.

16. Nebulous has two flowers per leaf axil, resulting in a very floriferous habit.

17. Nebulous will flower under the reduced light levels of the home thereby expanding the home market.

The accompanying colored photograph is a perspective view showing the overall appearance of Nebulous, with colors being as true as it is reasonably possible to obtain in a colored reproduction of this type. The photograph was taken in late June, 1988 with the plant being grown in a greenhouse.

The following is a detailed description of Nebulous based on plants produced under commercial practices in Ashtabula, Ohio under both greenhouse and outdoor growing conditions. Color references are made to The Royal Horticultural Society Colour Chart except where general terms of ordinary dictionary significance are used.

Parentage: A controlled cross between Mikkelsen Seedling No. 86-308-2 and Mikkelsen Seedling No. 85-196-3.

Propagation:

*Type cutting.*—Stem cutting 15 mm long will develop to 4 to 5 cm long in 18 to 21 days.

*Time to root.*—8 to 10 days at 23° C. summer, and 10 to 12 days at 20° C. winter.

*Rooting habit.*—Heavy, fibrous.

Plant description:

*Form.*—Semi-compact, symmetrically mounted.

*Habit of growth.*—Continuous flowering, excellent self-branching, and vigorous.

Foliage.—Purplish green leaves with red venation. No leaf variegation under normal light conditions. (1) Size: 10 to 12 cm in length and 3 to 4 cm wide at maturity. Environment can affect the size of the leaf. (2) Shape: Lanceolate with acuminate apex and acute. (3) Texture: Upper leaf surface slightly hirsute and lower surface is glabrous. (4) Margin: Entire and finely ciliated. (5) Color: Young foliage, top side: 146A. Under side: 183C. Mature foliage, top side: 148A, with purple underside providing a purple tinge. Under side: 183B. (6) Venation: Pinnate, red in color.

Flowering description:

*Flowering habits.*—Flowers continuously from leaf whorl in progressively orderly manner, with usually two flowers per axil. All first flowers from axil open before second flowers start to open at which time the first flowers of the whorl above start opening. It takes 5 to 7 days from mature bud to full open bloom and flowers last two weeks or longer.

*Natural flowering season.*—Indeterminant and continuous. Quantity of flowering increases with increasing levels of light.

*Flower buds.*—Ellipsoidal, flowers perfect. Reddish spur up to 3.5 cm long on mature bud with throat behind ovary and originating from the major sepal.

*Flowers borne.*—On individual pedicels from whorl of usually 5 leaves, flowering progressively around the whorl, with the second flower from an axial not opening until all first flowers have opened. Both first and second flowers are carried above foliage as internodes between whorls are short.

*Quantity of flowers.*—Very floriferous due to multiple flowering from axil and prolific self-branching of plant.

*Petals.*—(1) Shape: Heart shaped with upper petal the largest. (2) Color: Top side in summer when opening, 35A fading to 35C; under side 35B. (3) Number of petals: Five (5) in number. (4) Size of flowers: 5.5 to 6.0 cm in diameter.

Reproductive organs.—(1) Stamens: Five (5) in number. (a) Anther shape: Hooded, color cream with orange-red tint. (b) Pollen color: Cream. (2) Pistels: (a) Stigma shape: Segmented, column shaped; color, reddish purple tinge. (b) Style color: Purple. (c) Ovaries: Five (5) in number, size 5 mm, color, green with slight red tinge.

Disease resistance: No significant disease or insect problems noted to date.

I claim:

1. A new and distinct cultivar of Impatiens plant named Nebulous, as illustrated and described.

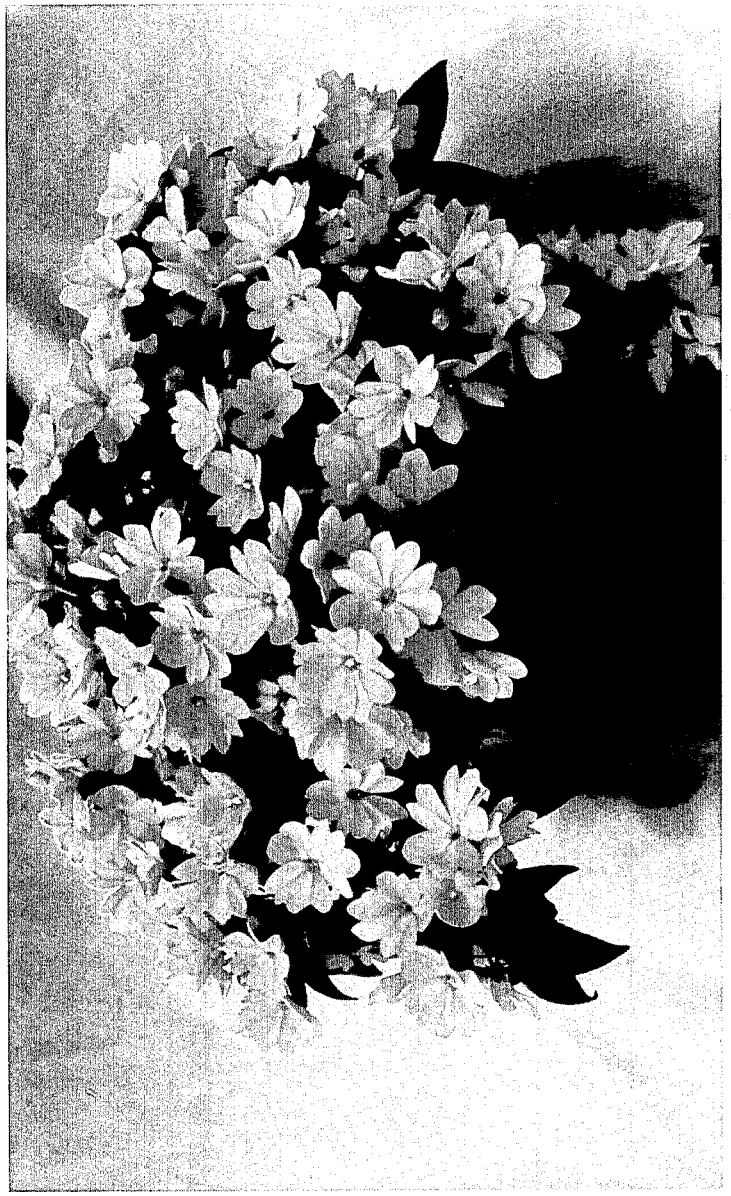

* * * * *